(12) United States Patent
Harding

(10) Patent No.: US 7,924,977 B2
(45) Date of Patent: Apr. 12, 2011

(54) METHODS, A PROCESSOR, AND A SYSTEM FOR IMPROVING AN ACCURACY OF IDENTIFICATION OF A SUBSTANCE

(75) Inventor: Geoffrey Harding, Hamburg (DE)

(73) Assignee: Morpho Detection, Inc., Newark, CA (US)

( * ) Notice: Subject to any disclaimer, the term of this patent is extended or adjusted under 35 U.S.C. 154(b) by 511 days.

(21) Appl. No.: 12/075,086

(22) Filed: Mar. 7, 2008

(65) Prior Publication Data

US 2009/0228216 A1    Sep. 10, 2009

(51) Int. Cl.
*G01N 23/20* (2006.01)
(52) U.S. Cl. ............................................ 378/71; 378/70
(58) Field of Classification Search .................... 378/70, 378/71, 82, 83, 86, 88, 90
See application file for complete search history.

(56) References Cited

U.S. PATENT DOCUMENTS

| 7,529,340 | B2 * | 5/2009 | Harding | 378/70 |
| 7,587,026 | B2 * | 9/2009 | Harding | 378/88 |
| 7,764,764 | B2 * | 7/2010 | Harding | 378/88 |
| 7,831,019 | B2 * | 11/2010 | Harding | 378/70 |
| 2007/0263770 | A1 | 11/2007 | Harding | |
| 2007/0263771 | A1 | 11/2007 | Harding | |
| 2007/0263772 | A1 | 11/2007 | Harding | |

FOREIGN PATENT DOCUMENTS

| EP | 1890135 A1 | 2/2008 |
| EP | 1884768 A2 | 6/2008 |
| EP | 2075572 A2 | 1/2009 |

OTHER PUBLICATIONS

B. D. Cullity and S. R. Stock. Elements of X-Ray Diffraction, third edition (New Jersey: Prentice Hall, 2001), p. 231-234.*
Geoffrey Harding, U.S. Appl. No. 11/541,716, "Systems and Methods for Classifying a Substance," filed Sep. 29, 2006.
Geoffrey Harding, U.S. Appl. No. 12/005,794, "Method, a Processor, and a System for Identifying a Substance," filed Dec. 28, 2007.
Geoffrey Harding et al., U.S. Appl. No. 12/005,843, "Systems and Methods for Reducing a Degradation Effect on a Signal," filed Dec. 28, 2007.
Geoffrey Harding, U.S. Appl. No. 12/006,010, "System and Methods for Characterizing a Substance," filed Dec. 28, 2007.
Geoffrey Harding, U.S. Appl. No. 12/006,140, "Method, a Processor, and a System for Tracking a Focus of a Beam," filed Dec. 31, 2007.
Harding, G, et al., Liquids identification with x-ray diffraction, Proceedings of the Spie- The International Society for the Optical Engineering, Spie, US, Sep. 24, 2007, pp. 67070T-1,XP002517126, vol. 6707.
Harding, Geoffrey, Effective density and atomic number determined from diffraction profiles, Proceedings of the Spie- The International Society for Optical Engineering, Spie, US, Aug. 30, 2006, pp. 631910-1, XP002459483, vol. 6139.
European Patent Office, European Search Report, Nov. 23, 2009, 7 pages, GHS/P512789EP.

* cited by examiner

*Primary Examiner* — Allen C. Ho
(74) *Attorney, Agent, or Firm* — Armstrong Teasdale LLP

(57) ABSTRACT

Methods, a processor, and a system for improving an accuracy of identification of a substance are described. One of the methods includes determining whether a relative molecular interference function of the substance includes at least one peak.

20 Claims, 7 Drawing Sheets

METHODS, A PROCESSOR, AND A SYSTEM FOR IMPROVING AN ACCURACY OF IDENTIFICATION OF A SUBSTANCE

FIELD OF THE INVENTION

The field of the invention relates generally to methods, a processor, and a system for identifying a substance and, more particularly, to methods, a processor, and a system for improving an accuracy of identification of the substance.

BACKGROUND OF THE INVENTION

The events of Sep. 11, 2001 instigated an urgency for more effective and stringent screening of airport baggage. The urgency for security expanded from an inspection of carry-on bags for knives and guns to a complete inspection of checked bags for a range of hazards with particular emphasis upon materials, such as, concealed explosives and narcotics.

X-ray baggage scanners are widely used for screening the baggage and identifying the materials. Identification systems based on X-ray diffraction (XRD) techniques provide an improved discrimination of the materials compared to that provided by the X-ray baggage scanners. The XRD identification systems measure d-spacings between lattice planes of micro-crystals in the materials. A "d-spacing" is a perpendicular distance between adjacent lattice planes in any of the materials.

However, the diffraction techniques suffer from a false alarm problem for some classes of substances. There are certain types of explosives in which an explosive component cannot be accurately identified by the XRD identification systems and the lack of identification leads to a high false alarm rate. Hence, an accuracy of the XRD identification systems in explosives detection and identifying the materials can be improved.

BRIEF DESCRIPTION OF THE INVENTION

A brief description of embodiments of methods, a processor, and a system for improving an accuracy of identification of a substance follows.

In one aspect, a method for improving an accuracy of identification of a substance is described. The method includes determining whether a relative molecular interference function of the substance includes at least one peak.

In another aspect, a processor is described. The processor is configured to determine whether a relative molecular interference function of a substance includes at least one peak.

In yet another aspect, a system for improving an accuracy of identification of a substance is described. The system includes an X-ray source configured to generate X-rays, and a detector operatively coupled to the X-ray source, configured to detect the X-rays and output an electrical signal representative of the detected X-rays. The system further includes a processor coupled to the detector and configured to determine whether a relative molecular interference function of the substance includes at least one peak.

In still another aspect, a method for improving an accuracy of identification of a substance is described. The method includes identifying the substance based on a peak variable of a peak of a characteristic function of the substance.

BRIEF DESCRIPTION OF THE DRAWINGS

FIG. 1 is an isometric view of an embodiment of a system for improving an accuracy of identification of a substance.

FIG. 2 is block diagram of an embodiment of a system used with the system of FIG. 1 for improving an accuracy of identification of a substance.

FIG. 3 is a flowchart of an embodiment of a method for improving an accuracy of identification of a substance.

FIG. 4 shows an embodiment of a diffraction profile of a substance used within the system of FIG. 1 and an embodiment of a diffraction profile of a calibration substance.

FIG. 5 is a continuation of the flowchart of FIG. 3.

FIG. 6 is a continuation of the flowchart of FIG. 5.

FIG. 7 shows an embodiment of a logarithmic diffraction profile of gasoline generated by using the systems of FIGS. 1 and 2.

FIG. 8 shows an embodiment of a logarithmic diffraction profile of sulphuric acid generated by using the systems of FIGS. 1 and 2.

FIG. 9 is a continuation of the flowchart of FIG. 6.

FIG. 10 is a continuation of the flowchart of FIG. 9.

FIG. 11 is a graph of an embodiment of a relative molecular interference function of an exemplary substance scanned by using the system of FIG. 1.

DETAILED DESCRIPTION OF THE INVENTION

While described in terms of detecting contraband including, without limitation, weapons, explosives, and/or narcotics, within baggage, the embodiments described herein can be used for any suitable diffraction imaging application.

Figure 1:
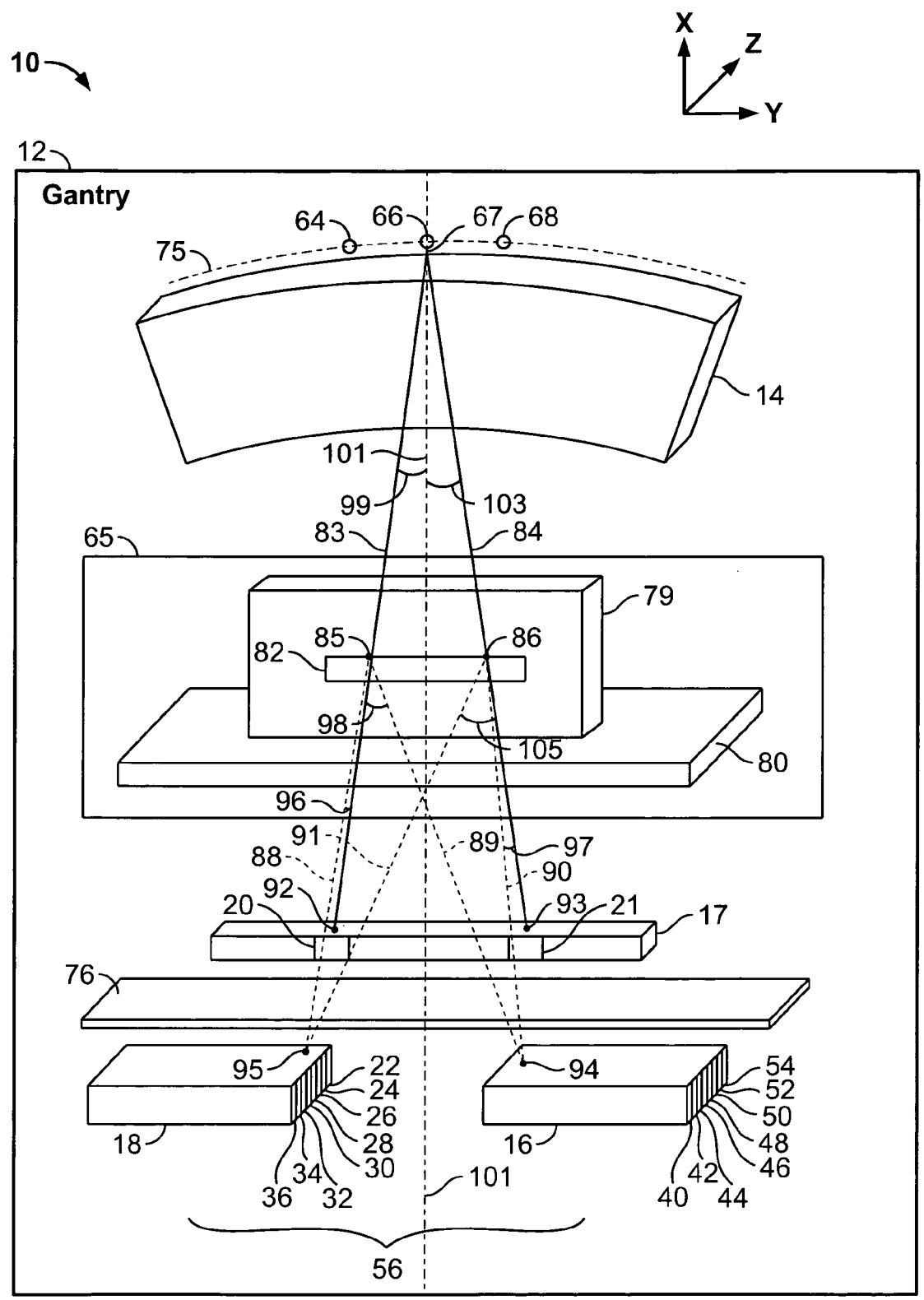
FIGS. 1-11 show embodiments of methods, a processor, and a system for improving an accuracy of identification of a substance.

FIG. 1 is an isometric view of an embodiment of a system 10 for improving an accuracy of identification of a substance. System 10 includes a gantry 12. Gantry 12 includes a primary collimator 14, which is a multi-focus primary collimator, a scatter detector 16, a transmission detector 17, a scatter detector 18, and a secondary collimator 76. Each scatter detector 16 and 18 is a segmented semiconductor detector.

Transmission detector 17 includes a plurality of detector elements, such as detector elements 20 and 21. Scatter detector 18 includes a plurality of detector cells or detector elements 22, 24, 26, 28, 30, 32, 34, and 36 for detecting coherent scatter. Scatter detector 16 includes a plurality of detector cells or detector elements 40, 42, 44, 46, 48, 50, 52, and 54 for detecting coherent scatter. Each scatter detector 16 and 18 includes any suitable number of detector elements, such as, ranging from and including 5 to 1200 detector elements. For example, scatter detector 18 includes 5 to 40 detector elements in a z-direction parallel to a z-axis, and 1 to 30 detector elements in a y-direction parallel to a y-axis. As another example, scatter detector 18 includes 5 detector elements in the z-direction and 1 detector element in the y-direction. As still another example, scatter detector 18 includes 20 detector elements in the z-direction, and 20 detector elements in the y-direction. As yet another example, scatter detector 18 includes 40 detector elements in the z-direction, and 30 detector elements in the y-direction. An x-axis, the y-axis, and the z-axis are located within an xyz co-ordinate system having an origin. The x-axis is perpendicular to the y-axis and the z-axis, the y-axis is perpendicular to the z-axis, and the x-axis is parallel to an x-direction. A number of detector elements within scatter detector 16 may be equal to a number of detector elements within scatter detector 18.

Scatter detector 16 is separate from scatter detector 18. For example, scatter detector 16 has a housing that is separate from a housing of scatter detector 18. As another example scatter detectors 16 and 18 are separated from each other by a gap. Each scatter detector 16, scatter detector 18, and transmission detector 17 is located in the same yz plane. The yz plane is formed by the y-axis and the z-axis.

Each scatter detector 16 and scatter detector 18 is separated from transmission detector 17 by a shortest distance ranging from and including 30 mm to 60 mm in the z-direction. As an example, scatter detector 18 is separated from transmission detector 17 by a shortest distance of 35 mm in the z-direction. As another example, scatter detector 18 is separated from transmission detector 17 by a shortest distance of 50 mm in the z-direction. As yet another example, scatter detector 18 is separated from transmission detector 17 by a shortest distance of 60 mm in the z-direction.

Gantry 12 further includes a plurality of X-ray sources 64, 66, and 68. X-ray sources 64, 66, and 68, and transmission detector 17 form an inverse single-pass multi-focus imaging system. X-ray sources 64, 66, and 68 have an inverse fan-beam geometry that includes a symmetric location of the X-ray sources 64, 66, and 68 relative to the z-axis. X-ray sources 64, 66, and 68, are located parallel to and coincident with an arc 75. Each X-ray source 64, 66, and 68 is an X-ray source that includes a cathode and an anode. Alternatively, each X-ray source 64, 66, and 68 is an X-ray source that includes a cathode and all X-ray sources 64, 66, and 68 share a common anode.

A container 79 is placed on a support 80 between a set of X-ray sources 64, 66, and 68, and a set of scatter detectors 16 and 18. Container 79 and support 80 are located within an opening 65 of gantry 12. Examples of container 79 include, but are not limited to, a bag, a box, and an air cargo container. Examples of each X-ray source 64, 66, and 68 include, but are not limited to, a polychromatic X-ray source. Container 79 includes a substance 82. Non-limiting examples of substance 82 include an organic explosive, an amorphous substance having a crystallinity of less than twenty five percent, a quasi-amorphous substance having a crystallinity at least equal to twenty-five percent and less than fifty percent, and a partially crystalline substance having a crystallinity at least equal to fifty percent and less than one-hundred percent. A gel explosive is a non-limiting example of the amorphous substance, a slurry explosive is a non-limiting example of the quasi-amorphous substance, and a special nuclear material and an explosive including ammonium nitrate are non-limiting examples of the partially crystalline substance. Non-limiting examples of the special nuclear material include plutonium and uranium. Non-limiting examples of support 80 include a table and a conveyor belt. An example of each scatter detector 16 and 18 includes a segmented detector fabricated from Germanium.

X-ray source 66 emits an X-ray beam 67 in an energy range, which is dependent on a voltage applied by a power source to X-ray source 66. Primary collimator 14 generates two primary beams 83 and 84, such as pencil beams, upon collimating X-ray beam 67 from X-ray source 66. In an alternative embodiment, primary collimator 14 collimates X-ray beam 67 received from X-ray source 66 to generate a plurality, such as three or four, primary beams. A number of primary beams generated by primary collimator 14 is equal to or alternatively greater than a number of scatter detectors on one side of transmission detector 17 and on one side of the y-axis. Primary beams 83 and 84 pass through a plurality of points 85 and 86 on substance 82 within container 79 arranged on support 80 to generate scattered radiation 88, 89, 90, and 91. For example, primary beam 83 passes through point 85 to generate scattered radiation 88 and 89. As another example, primary beam 84 passes through point 86 to generate scattered radiation 90 and 91.

Secondary collimator 76 is located between support 80 and scatter detectors 16 and 18. Secondary collimator 76 includes a number of collimator elements, such as sheets, slits, or laminations, to ensure that scattered radiation arriving at scatter detectors 16 and 18 have constant scatter angles with respect to primary beams 83 and 84 and that a position of scatter detectors 16 and 18 permits a depth in container 79 at which the scattered radiation originated to be determined. For example, the collimator elements of secondary collimator 76 are arranged parallel to a direction of scattered radiation 88 and of scattered radiation 90 to absorb scattered radiation that is not parallel to the direction of scattered radiation 88 and of scattered radiation 90.

The number of collimator elements in secondary collimator 76 is equal to or alternatively greater than a number of detector elements of scatter detectors 16 and/or 18. The collimator elements are arranged such that scattered radiation between neighboring collimator elements is incident on one of the detector elements. The collimator elements of scatter detectors 16 and 18 are made of a radiation-absorbing material, such as steel, copper, silver, or tungsten.

Transmission detector 17 is positioned underneath support 80. The transmission detector 17 is configured to measure an intensity of primary beam 83 at a point 92 on transmission detector 17 and to measure an intensity of primary beam 84 at a point 93 on transmission detector 17. Moreover, scatter detectors 16 and 18 that measure photon energies of scattered radiation are positioned underneath support 80. The scatter detectors 16 and 18 are each configured to measure photon energies of received scattered radiation. Each scatter detector 16 and 18 measures the X-ray photons within scattered radiation received by scatter detectors 16 and 18 in an energy-sensitive manner by outputting a plurality of electrical output signals linearly dependent on a plurality of energies of the X-ray photons detected from within the scattered radiation. Scatter detector 16 measures scattered radiation 90 received at a point 94 on scatter detector 16 and scatter detector 18 measures scattered radiation 88 received at a point 95 on scatter detector 18.

Scatter detectors 16 and 18 detect scattered radiation to generate a plurality of electrical output signals. Scatter detector 16 detects scattered radiation 90 generated upon intersection of primary beam 84 with point 86. Moreover, scatter detector 16 detects at least a portion of scattered radiation 89 generated upon intersection of primary beam 83 with point 85. Scatter detector 18 detects scattered radiation 88 generated upon intersection of primary beam 83 with point 85. Moreover, scatter detector 18 detects at least a portion of scattered radiation 91 generated upon intersection of primary beam 84 with point 86.

A scatter angle 96 formed between primary beam 83 and scattered radiation 88 is equal to a scatter angle 97 formed between primary beam 84 and scattered radiation 90. An example of each scatter angle 96 and 97 includes an angle ranging from and including 0.025 radians to 0.045 radians. As another example, each scatter angle 96 and 97 includes an angle of 0.03 radians. As yet another example, each scatter angle 96 and 97 includes an angle of 0.04 radians. As still another example, each scatter angle 96 and 97 includes an angle of 0.045 radians. An example of a scatter angle 98 formed between primary beam 83 and scattered radiation 89 ranges from and including 0.05 radians to 0.09 radians. An example of scatter angle 98 includes 0.05 radians. Another example of scatter angle 98 includes 0.07 radians. Yet another example of scatter angle 98 includes 0.09 radians. Moreover, an example of a scatter angle 105 formed between primary beam 84 and scattered radiation 91 ranges from and including 0.05 radians to 0.09 radians. An example of scatter angle 105 includes 0.05 radians. Another example of scatter angle 105 includes 0.07 radians. Yet another example of scatter angle 105 includes 0.09 radians. Scatter angle 98 is at least two times greater than scatter angles 96 and/or 97 and scatter angle 105 is at least two times greater than scatter angles 96 and/or 97. An angle 99 formed by primary beam 83 with respect to a center line 101 between scatter detectors 16 and 18 is equal to an angle 103 formed by primary beam 84 with respect to center line 101. Center line 101 passes through X-ray source 66.

In an alternative embodiment, system 10 includes additional scatter detectors other than scatter detectors 16 and 18. The additional scatter detectors are placed on a side of transmission detector 17 that includes scatter detectors 16 and 18. Moreover, the additional scatter detectors are the same as scatter detectors 16 and 18. For example, any one of the additional scatter detectors has the same number of detector elements as that of scatter detectors 16 and/or 18. In yet another alternative embodiment, system 10 does not include scatter detector 16. In still another alternative embodiment, a single-focus primary collimator is used instead of primary collimator 14. In an alternative embodiment, gantry 12 includes any number, such as one, two, four, five, or ten X-ray sources.

Figure 2:
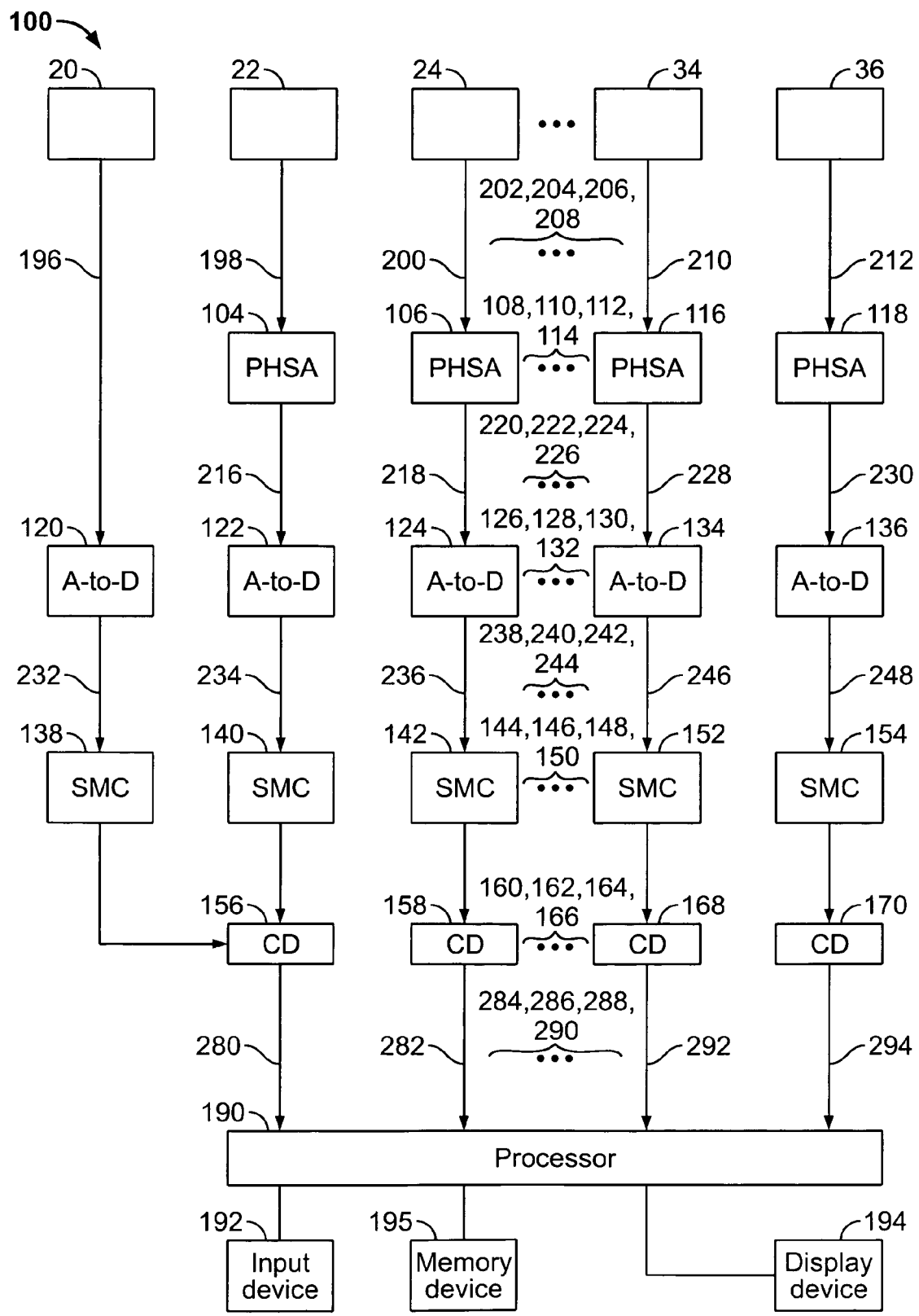

FIG. 2 is block diagram of an embodiment of a system 100 for improving an accuracy of identification of a substance. System 100 includes detector element 20 of transmission detector 17, scatter detector elements 22, 24, 26, 28, 30, 32, 34, and 36, a plurality of pulse-height shaper amplifiers (PHSA) 104, 106, 108, 110, 112, 114, 116, and 118, a plurality of analog-to-digital (A-to-D) converters 120, 122, 124, 126, 128, 130, 132, 134, and 136, a plurality of spectrum memory circuits (SMCs) 138, 140, 142, 144, 146, 148, 150, 152, and 154 allowing pulse height spectra to be acquired, a plurality of correction devices (CDs) 156, 158, 160, 162, 164, 166, 168, and 170, a processor 190, an input device 192, a display device 194, and a memory device 195. As used herein, the term processor is not limited to just those integrated circuits referred to in the art as a processor, but broadly refers to a computer, a microcontroller, a microcomputer, a programmable logic controller, an application specific integrated circuit, and any other programmable circuit. The computer may include a device, such as, a floppy disk drive or CD-ROM drive, for reading data including the methods for improving an accuracy of identification of a substance from a computer-readable medium, such as a floppy disk, a compact disc-read only memory (CD-ROM), a magneto-optical disk (MOD), and/or a digital versatile disc (DVD). In an alternative embodiment, processor 190 executes instructions stored in firmware. Non-limiting examples of display device 194 include a liquid crystal display (LCD) and a cathode ray tube (CRT). Non-limiting examples of input device 192 include a mouse and a keyboard. Non-limiting examples of memory device 195 include a random access memory (RAM) and a read-only memory (ROM). An example of each correction device 156, 158, 160, 162, 164, 166, 168, and 170 include a divider circuit. Each spectrum memory circuit 138, 140, 142, 144, 146, 148, 150, 152, and 154 includes an adder and a memory device, such as a RAM or a ROM.

Detector element 20 is coupled to analog-to-digital converter 120, and detector elements 22, 24, 26, 28, 30, 32, 34, and 36 are coupled to pulse-height shaper amplifiers 104, 106, 108, 110, 112, 114, 116, and 118, respectively. Detector element 20 generates an electrical output signal 196 by detecting primary beam 83 and detector elements 22, 24, 26, 28, 30, 32, 34, and 36 generate a plurality of electrical output signals 198, 200, 202, 204, 206, 208, 210, and 212 by detecting scattered radiation. For example, detector element 22 generates electrical output signal 198 for each scattered X-ray photon incident on detector element 22. Each pulse-height shaper amplifier amplifies an electrical output signal received from a corresponding detector element. For example, pulse-height shaper amplifier 104 amplifies electrical output signal 198 and pulse-height shaper amplifier 106 amplifies electrical output signal 200. Pulse-height shaper amplifiers 104, 106, 108, 110, 112, 114, 116, and 118 have a gain factor determined by processor 190.

An amplitude of an electrical output signal output from a detector element is proportional to an energy of an X-ray quantum that is detected by the detector element to generate the electrical output signal. For example, an amplitude of electrical output signal 196 is proportional to an energy of an X-ray quantum in primary beam 83 detected by detector element 20. As another example, an amplitude of electrical output signal 198 is proportional to an energy of an X-ray quantum within scattered radiation that is detected by detector element 22.

A pulse-height shaper amplifier generates an amplified output signal by amplifying an electrical output signal generated from a detector element. For example, pulse-height shaper amplifier 104 generates an amplified output signal 216 by amplifying electrical output signal 198 and pulse-height shaper amplifier 106 generates an amplified output signal 218 by amplifying electrical output signal 200. Similarly, a plurality of amplified output signals 220, 222, 224, 226, 228, and 230 are generated.

An analog-to-digital converter converts an output signal from an analog form to a digital form to generate a digital output signal. For example, analog-to-digital converter 120 converts electrical output signal 196 from an analog form to a digital format to generate a digital output signal 232 and analog-to-digital converter 122 converts amplified output signal 216 from an analog form to a digital format to generate a digital output signal 234. Similarly, a plurality of digital output signals 236, 238, 240, 242, 244, 246, and 248 are generated by analog-to-digital converters 124, 126, 128, 130, 132, 134, and 136, respectively. A digital value of a digital output signal generated by an analog-to-digital converter represents an amplitude of energy of a pulse of an amplified output signal. For example, a digital value of digital output signal 234 output by analog-to-digital converter 122 is a value of an amplitude of a pulse of amplified output signal 216. Each pulse is generated by an X-ray quantum, such as an X-ray photon.

An adder of a spectrum memory circuit adds a number of pulses in a digital output signal. For example, when analog-to-digital converter 122 converts a pulse of amplified output signal 216 into digital output signal 234 to determine an amplitude of the pulse of amplified output signal 216, an adder within spectrum memory circuit 140 increments, by one, a value within a memory device of spectrum memory circuit 140. Accordingly, at an end of an X-ray examination of substance 82, a memory device within a spectrum memory circuit stores a number of X-ray quanta detected by a detector element. For example, a memory device within spectrum memory circuit 142 stores a number of X-ray photons detected by detector element 24 and each of the X-ray photons has an amplitude of energy or alternatively an amplitude of intensity that is determined by analog-to-digital converter 124.

A correction device receives a number of X-ray quanta that have a range of energies and are stored within a memory device of one of spectrum memory circuits 140, 142, 144, 146, 148, 150, 152, and 154, and divides the number of X-ray quanta by a number of X-ray quanta having the range of energies received from a memory device of spectrum memory circuit 138. For example, correction device 156 receives a number of X-ray photons having a range of energies from a memory device of spectrum memory circuit 140, and divides the number by a number of X-ray photons having the range received from a memory device of spectrum memory circuit 138. Each correction device outputs a correction output signal that represents a range of energies within X-ray quanta received by a detector element. For example, correction device 156 outputs a correction output signal 280 representing an energy spectrum or alternatively an intensity spectrum within X-ray quanta detected by detector element 22. As another example, correction device 158 outputs correction output signal 282 representing an energy spectrum within X-ray quanta detector element 24. Similarly, a plurality of correction output signals 284, 286, 288, 290, 292, and 294 are generated by correction devices 160, 162, 164, 166, 168, and 170, respectively.

It is noted that a number of pulse-height shaper amplifiers 104, 106, 108, 110, 112, 114, 116, and 118 changes with a number of scatter detector elements 22, 24, 26, 28, 30, 32, 34, and 36. For example, five pulse-height shaper amplifiers are used for amplifying signals received from five corresponding scatter detector elements. As another example, four pulse-height shaper amplifiers are used for amplifying signals received from four corresponding scatter detector elements. Similarly, a number of analog-to-digital converters 120, 122, 124, 126, 128, 130, 132, 134, and 136 changes with a number of detector elements 20, 22, 24, 26, 28, 30, 32, 34, and 36 and a number of spectrum memory circuits 138, 140, 142, 144, 146, 148, 150, 152, and 154 changes with the number of detector elements 20, 22, 24, 26, 28, 30, 32, 34, and 36.

Processor 190 receives correction output signals 280, 282, 284, 286, 288, 290, 292, and 294 to generate a momentum transfer x, measured in inverse nanometers ($nm^{-1}$), from an energy spectrum r(E) of energy E of X-ray quanta within scattered radiation detected by scatter detector 18 (shown in FIG. 1). Substance 82 is unknown at the time of scanning of substance 82 and the scan is performed to generate electrical output signals 196, 198, 200, 202, 204, 206, 208, 210, and 212. Processor 190 generates the momentum transfer x by applying $$x=(E/hc)\sin(\theta/2) \qquad \text{Eq. (1)}$$

where c is a speed of light, h is Planck's constant, θ represents a constant scatter angle of X-ray quanta of scattered radiation detected by scatter detector 18 (shown in FIG. 1). Non-limiting examples of θ include scatter angles 96 and 97 (shown in FIG. 1). Processor 190 relates the energy E to the momentum transfer x by Eq. (1). Mechanical dimensions of secondary collimator 76 (shown in FIG. 1) defines the scatter angle θ. The secondary collimator 76 (shown in FIG. 1) restricts scattered radiation that does not have the scatter angle θ. Processor 190 receives the scatter angle θ from a user, such as a human being, via input device 192. Processor 190 generates a diffraction profile of substance 82 (shown in FIG. 1) by calculating a number of scatter X-ray photons that are detected by scatter detector 18 and by plotting the number of X-ray photons versus the momentum transfer x.

Figure 3:
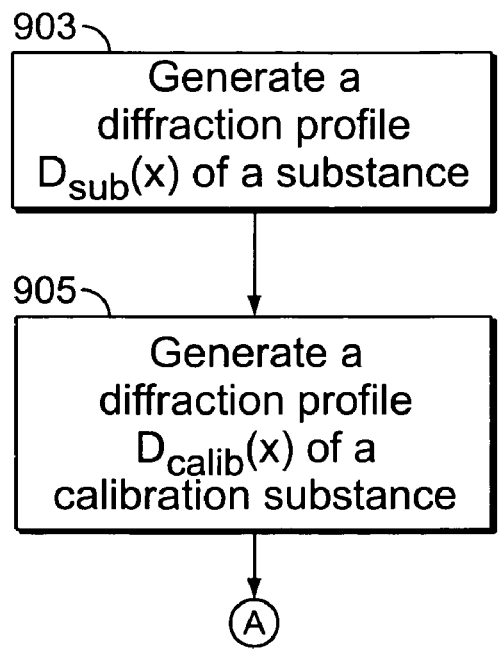
Figure 4:
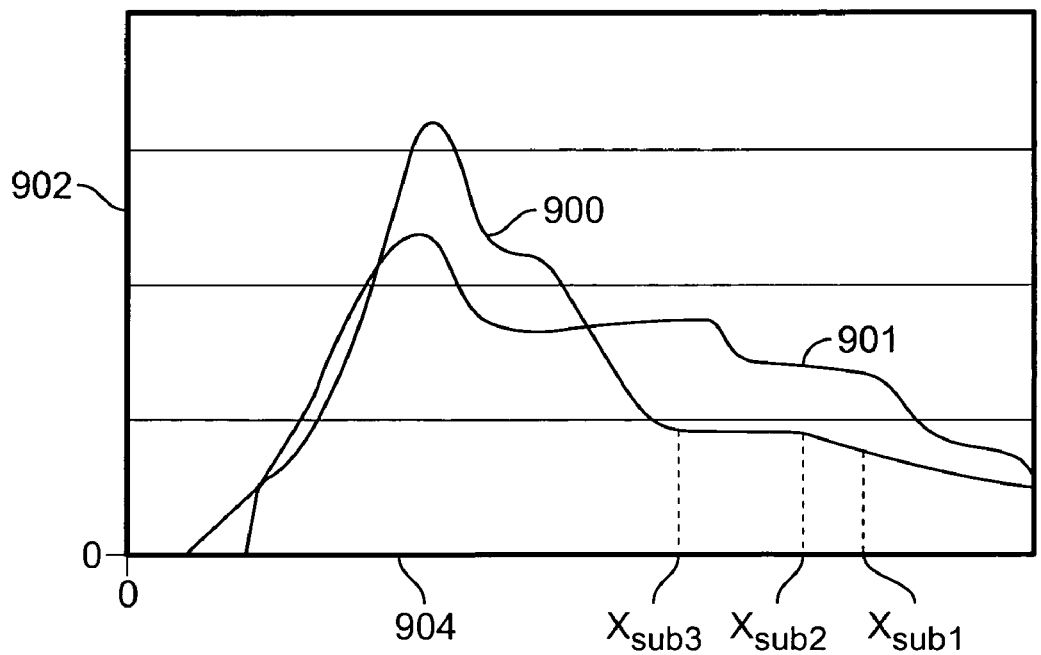

FIG. 3 is a flowchart of an embodiment of a method for improving an accuracy of identification of a substance and FIG. 4 shows a plurality of graphs 900 and 901. Graph 900 is a diffraction profile $D_{sub}(x)$ of substance 82 that is generated 903 by processor 190. Graph 900 is a histogram having a plurality of intensity values at a plurality of momentum transfer values, such as $x_{sub1}$, $x_{sub2}$, and $x_{sub3}$, of the momentum transfer x. As an example, when an operating voltage of X-ray source 66 is 160 kilovolts (kV), processor 190 calculates, by applying Equation (1), an energy value $E_1$ of the energy E to be 160 keV, calculates, by applying Equation (1), an energy value $E_2$ of the energy E to be 140 keV, and calculates, by applying Equation (1), an energy value $E_3$ of the energy value E to be photon energy 120 keV. In this example, the photon energy values $E_1$, $E_2$, and $E_3$ correspond, through Equation (1), to $x_{sub1}$ of four inverse nanometers, to $x_{sub2}$ of 3.5 inverse nanometers, and to $x_{sub3}$ of three inverse nanometers, respectively. Graph 900 represents a histogram of a number of X-ray photons detected by scatter detector 18 versus the momentum transfer x of the X-ray photons when substance 82 is placed within system 10.

Graph 901 is a diffraction profile $D_{calib}(x)$ of a calibration substance, such as a white scatterer. An example of the white scatterer includes a combination of Lucite chippings, Cellulose paste, and water. The diffraction profile $D_{calib}(x)$ of the calibration substance is generated 905 in a similar manner as generation 903 of $D_{sub}(x)$. For example, the white scatterer is placed periodically, such as once each month or every 15 days, on a table within an object space, such as opening 65, of system 10, and is moved within the object space. In the example, upon scanning the white scatterer, a plurality of correction output signals are generated by system 100 (shown in FIG. 2) that is connected to scatter detector 18, and processor 190 generates the diffraction profile $D_{calib}(x)$ representing a number of photons detected by scatter detector 18 versus the momentum transfer x. Graph 901 represents a histogram of a number of X-ray photons detected by scatter detector 18 versus the momentum transfer x of the X-ray photons when the calibration substance is placed within system 10.

A number of X-ray photons detected by scatter detector 18 is plotted along an ordinate 902 and a momentum transfer x is plotted along an abscissa 904. As an example, abscissa 904 extends from and includes zero inverse nanometers ($nm^{-1}$) to 10 $nm^{-1}$. An example of a total number of bins of numbers of X-ray photons plotted on ordinate 902 lies between 64 and 1024. An example of a number of X-ray photons detected by each scatter detector 16 and 18 per examination lies between 1000 and 100,000.

The diffraction profile $D_{sub}(x)$ ranging from $x \geq 3$ $nm^{-1}$ is generally dominated by coherent scatter from free atoms of substance 82. In a tip region, extending from $x_{sub1}$ to $x_{sub3}$, of graph 900, an intensity of scattered radiation is proportional to a product of density, such as a mean density, of substance 82 and a power, such as ranging between 2.5 and 3.5, of a mean atomic number of a plurality of materials within substance 82.

Figure 5:
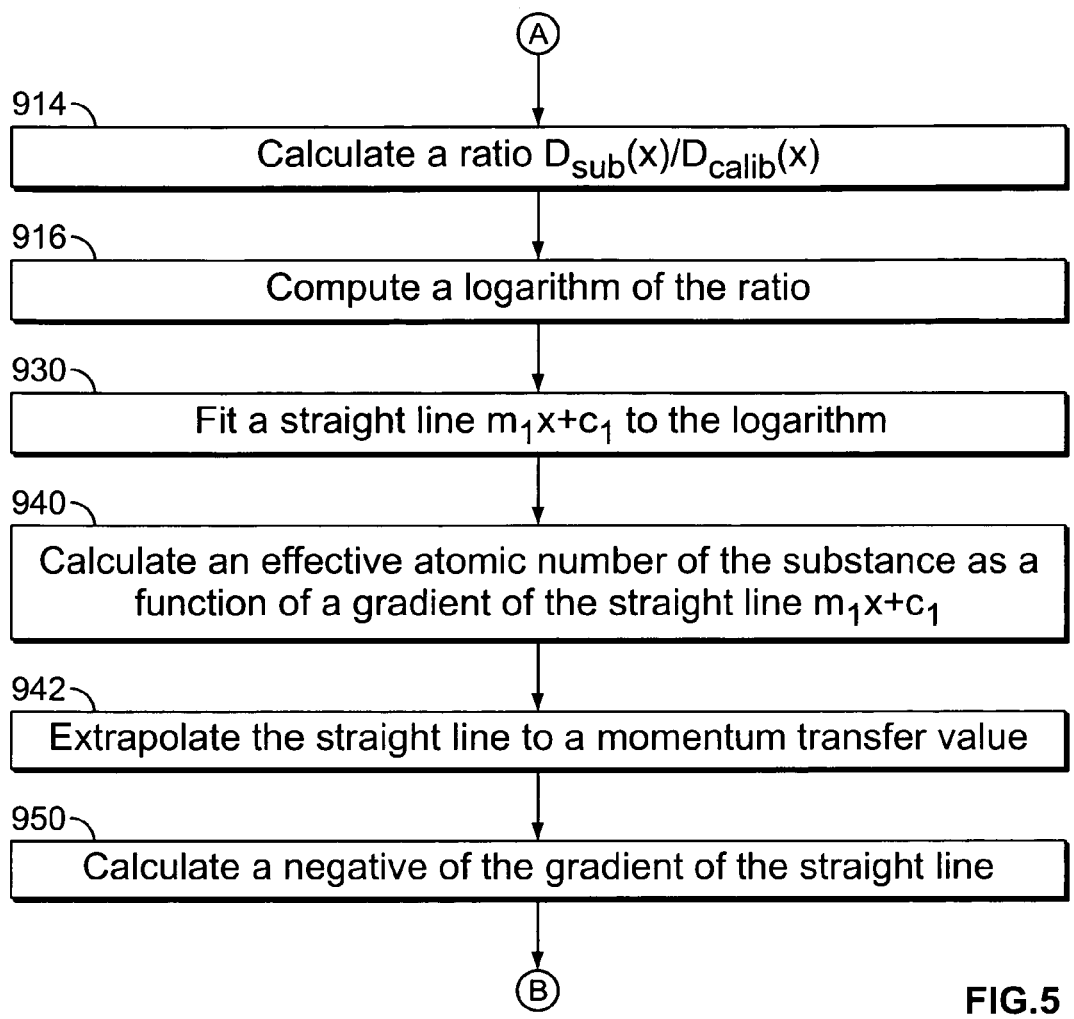
Figure 7:
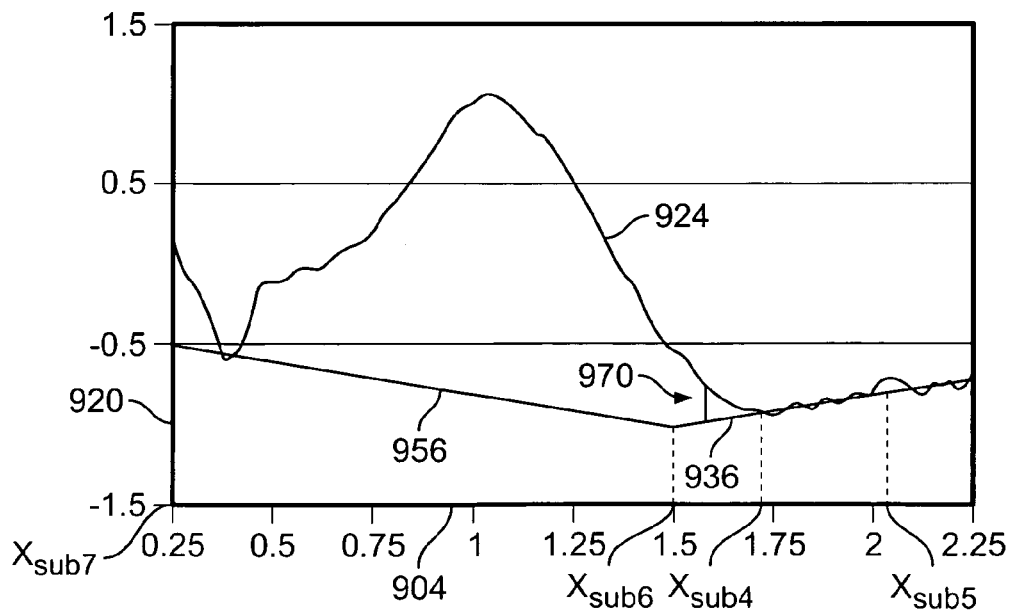
Figure 6:
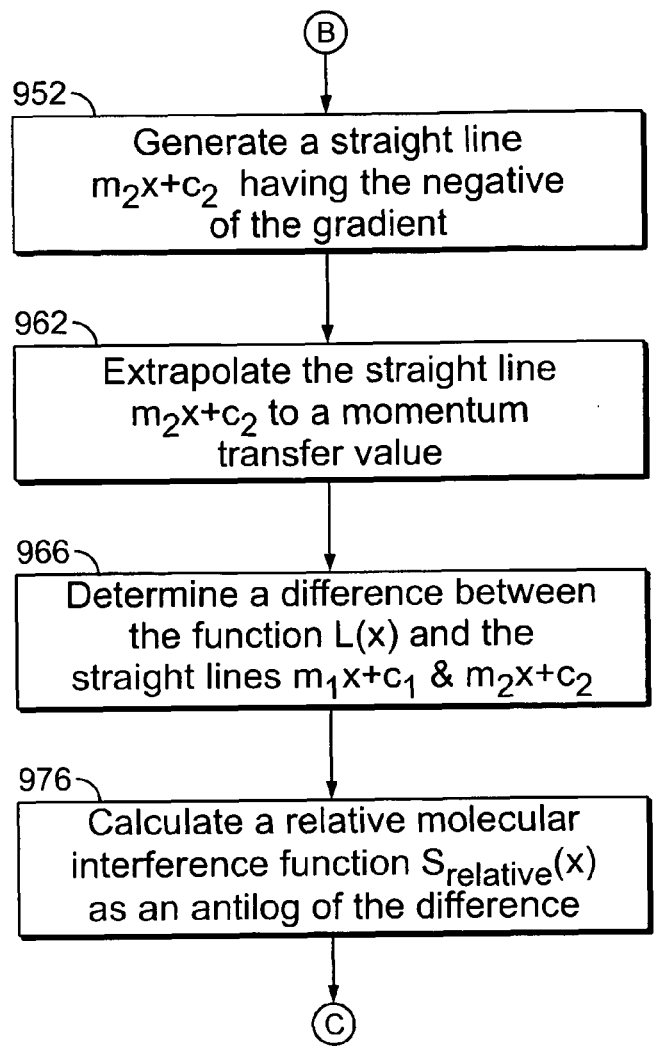
Figure 8:
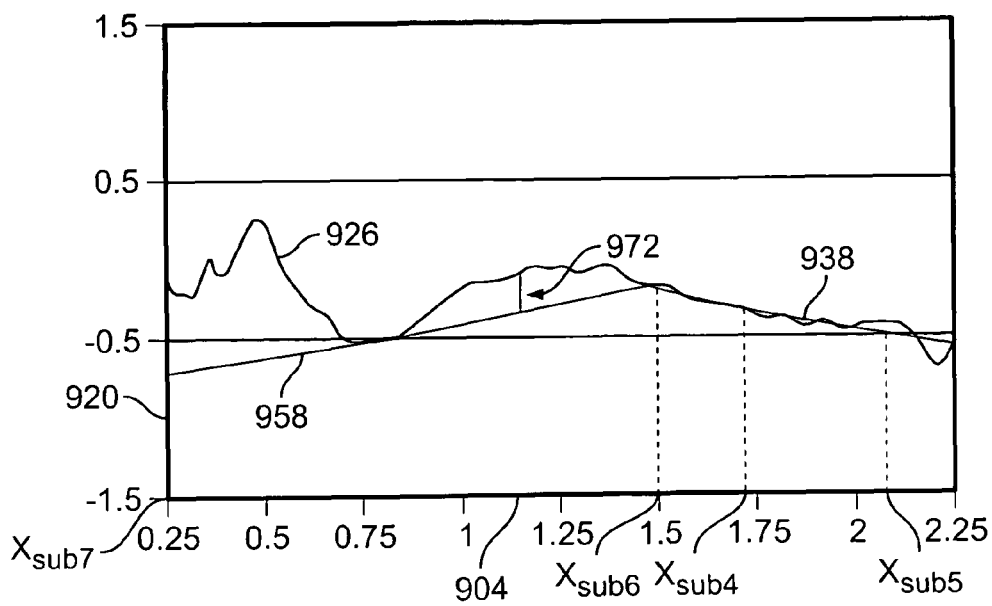

FIGS. 5 and 6 are a flowchart of an embodiment of a method for improving an accuracy of identification of a substance and FIGS. 7 and 8 show a plurality of graphs 924 and 926. Referring to FIG. 5, processor 190 calculates 914 a ratio $D_{sub}(x)/D_{calib}(x)$ of the diffraction profiles 900 and 901. The ratio $D_{sub}(x)/D_{calib}(x)$ is a normalized profile. Processor 190 further computes 916 a logarithm of the ratio $D_{sub}(x)/D_{calib}(x)$ as a function $$L_{sub}(x)=\log_e[D_{sub}(x)/D_{calib}(x)] \qquad \text{Eq. (2)}$$

where the function $L_{sub}(x)$ is a logarithmic profile ratio.

Graph 924, of FIG. 7, is a function $L_{gas}(x)$ and an example of the function $L_{sub}(x)$. Processor 190 generates graph 924 as a logarithm, to the base e, of a ratio of a diffraction profile $D_{gas}(x)$ of gasoline and the diffraction profile $D_{calib}(x)$ versus the momentum transfer x. Gasoline, referred to herein as gas, is an example of substance 82. Processor 190 plots $\log_e[D_{gas}(x)/D_{calib}(x)]$ on an ordinate 920 and plots the momentum transfer x on abscissa 904.

Graph 926, of FIG. 8, is a function $L_{sulphuric}(x)$ and an example of the function $L_{sub}(x)$. Processor 190 generates graph 926 as a logarithm, to the base e, of a ratio of a diffraction profile $D_{sulphuric}(x)$ of sulphuric acid ($H_2SO_4$) and the diffraction profile $D_{calib}(x)$ versus the momentum transfer x. Sulphuric acid is an example of substance 82. Processor 190 plots $\log_e[D_{sulphuric}(x)/D_{calib}(x)]$ on ordinate 920 and plots the momentum transfer x on abscissa 904.

Referring back to FIG. 5, processor 190 fits 930 a straight line $m_1x+c_1$ to at least one value of $L_{sub}(x)$ within a range from and including $x_{sub4}$ to $x_{sub5}$ of the function $L_{sub}(x)$, where $m_1$ is a gradient of the straight line and $c_1$ is an intercept of the straight line with ordinate 920, $m_1$ may be a positive or a negative number, and $c_1$ may be a positive or negative number. An example of $x_{sub4}$ includes 1.5 $nm^{-1}$. Another example of $x_{sub4}$ includes 1.7 $nm^{-1}$. An example of $x_{sub5}$ includes 2.1 $nm^{-1}$. Another example of $x_{sub5}$ includes 2.3 $nm^{-1}$. As an example, processor 190 fits a straight line 936 (shown in FIG. 7) to all values of $L_{gas}(x)$ within a range from and including $x_{sub4}$ to $x_{sub5}$. As another example, processor 190 fits a straight line 938 (shown in FIG. 8) to all values of $L_{sulphuric}(x)$ within a range from and including $x_{sub4}$ to $x_{sub5}$. As still another example, processor 190 fits the straight line $m_1x+c_1$ to all values of $L_{sub}(x)$ within a range from and including $x_{sub4}$ to $x_{sub5}$ by applying a linear regression fit to the values. As another example, processor 190 fits the straight line $m_1x+c_1$ to all values of $L_{sub}(x)$ within a range from and including $x_{sub4}$ to $x_{sub5}$ by applying a weighted linear regression fit. In applying the weighted linear regression fit, processor 190 applies a higher weight to some of the values of $L_{sub}(x)$ within a range from and including $x_{sub4}$ to $x_{sub5}$ that are less noisy than to the remaining of the values that are more noisy. As yet another example, processor 190 divides all values of $L_{sub}(x)$ within a range from and including $x_{sub4}$ to $x_{sub5}$ into two windows. Processor 190 averages values of $L_{sub}(x)$ within each window and fits the straight line $m_1x+c_1$ to the two average values. Each straight line 936 and 938 is an example of the straight line $m_1x+c_1$.

Processor 190 may fit the straight line $m_1x+c_1$ by applying a least squares fit approach. As another example, processor 190 determines the straight line $m_1x+c_1$ that fits all values of $L_{sub}(x)$ between $x_{sub4}$ and $x_{sub5}$ by minimizing a sum of squares of perpendicular distances between the straight line and the values. As yet another example, processor 190 determines the straight line $m_1x+c_1$ that fits all values of $L_{sub}(x)$ between $x_{sub4}$ and $x_{sub5}$ by minimizing a sum of squares of vertical distances between the straight line and the values. As yet another example, processor 190 fits the straight line $m_1x+c_1$ to $L_{sub}(x)$ by determining that the straight line is connected to $L_{sub}(x)$ at $x_{sub4}$ and at $x_{sub5}$.

Processor 190 calculates 940 an effective atomic number $Z_{effsub}$ of substance 82 as a function of the gradient $m_1$ by applying $$m_1 = F(Z_{effsub}, Z_{effcalib}), \quad \text{Eq. (3)}$$

where $Z_{effcalib}$ is an effective atomic number of the calibration substance. Processor 190 receives the $Z_{effcalib}$ from a user via input device 192 and stores the $Z_{effcalib}$ in memory device 195. An example of $Z_{effcalib}$ is an atomic number of nitrogen. Another example of $Z_{effcalib}$ is an effective atomic number of the white scatterer.

Processor 190 determines the function F from substances with known effective atomic numbers. For example, a substance with known effective atomic number $Z_{known1}$ is scanned by using system 10 in the same manner as that of substance 82 to generate a plurality of electrical output signals, which are received from scatter detector 18. The substance with effective atomic number $Z_{known1}$ is a known substance. An example of the effective atomic number $Z_{known1}$ includes an atomic number of six for carbon. Another example of the effective atomic number $Z_{known1}$ includes an atomic number of eight for oxygen.

Processor 190 of system 100 receives a plurality of signals from scatter detector 18 and executes 903 (shown in FIG. 3) on the known substance instead of substance 82 to generate a diffraction profile $D_{known1}(x)$ of the known substance. Processor 190 further calculates a ratio $D_{known1}(x)/D_{calib}(x)$ instead of calculating 914 ratio $D_{sub}(x)/D_{calib}(x)$, computes a $\log_e(D_{known1}(x)/D_{calib}(x))$ instead of computing 916 $\log_e(D_{sub}(x)/D_{calib}(x))$, and fits a straight line to at least one value of the ratio $\log_e(D_{known1}(x)/D_{calib}(x))$ between $x_{sub4}$ and $x_{sub5}$ instead of fitting 930, determines a gradient $m_{known1}$ of the straight line, and determines that the gradient $m_{known1}$ is a function $F_{known1}$, such as a best fit function, of the two effective atomic numbers $Z_{known1}$ and $Z_{effcalib}$. The function $F_{known1}$ corresponds to the effective atomic number $Z_{known1}$.

Processor 190 also determines a plurality of additional functions $F_{known2}, F_{known3}, F_{known4}, \ldots, F_{knownN}$ of N known substances with corresponding effective atomic numbers $Z_{known2}, Z_{known3}, \ldots, Z_{knownN}$ in the same manner as that of determining $Z_{known1}$ and creates a list of the functions $F_{known1}, F_{known2}, F_{known3}, F_{known4}, \ldots, F_{knownN}$ versus known effective atomic numbers $Z_{known1}, Z_{known2}, \ldots, Z_{knownN}$, where N is an integer. Processor 190 determines the function F as a relationship, such as linear or polynomial, between the functions $F_{known1}, F_{known2}, F_{known3}, F_{known4}, \ldots, F_{knownN}$ and the known effective atomic numbers $Z_{known1}, Z_{known2}, \ldots, Z_{knownN}$.

Processor 190 determines an inverse function $F^{-1}$ and calculates 940 the effective atomic number $Z_{effsub}$ as a function of $m_1$ and $Z_{effcalib}$. For example, processor 190 calculates the effective atomic number $Z_{effsub}$ as $F^{-1}(m_1) + Z_{effcalib}$, where $F^{-1}$ is the inverse of the function F. Processor 190 extrapolates 942 the straight line $m_1x+c_1$ from $x_{sub4}$ to a momentum transfer value $x_{sub6}$, shown in FIGS. 7 and 8. For example, processor 190 extrapolates straight line 938 (shown in FIG. 8) from $x_{sub4}$ to $x_{sub6}$. As another example, processor 190 extrapolates straight line 936 (shown in FIG. 7) from $x_{sub4}$ to $x_{sub6}$. An example of $x_{sub6}$ includes 1.5 $nm^{-1}$. Another example of $x_{sub6}$ includes 1.3 $nm^{-1}$. Another example of $x_{sub6}$ includes 2 $nm^{-1}$. Yet another example of $x_{sub6}$ includes $x_{sub4}$ in which case processor 190 does not need to extrapolate the straight line $m_1x+c_1$ from $x_{sub4}$ to $x_{sub6}$.

Processor 190 calculates 950 a negative of the gradient $m_1$ and generates 952 a straight line $m_2x+c_2$, where $m_2$ is a gradient of the straight line and $c_2$ is an intercept of the straight line with ordinate 920. As an example, $m_2 = -m_1$. As another example, $m_2 = -1.1\, m_1$. An example of the straight line $m_2x+c_2$ is shown as a straight line 956 in FIG. 7. Another example of the straight line $m_2x+c_2$ is shown as a straight line 958 in FIG. 9B.

Processor 190 extrapolates 962 the straight line $m_2x+c_2$ from $x_{sub6}$ to a momentum transfer value $x_{sub7}$ shown in FIGS. 7 and 8. An example of $x_{sub7}$ is 0 $nm^{-1}$. Another example of $x_{sub7}$ is 0.25 $nm^{-1}$. Processor determines 966 a difference between the function $L_{sub}(x)$ and a set of the straight lines $m_1x+c_1$ and $m_2x+c_2$. For example, processor 190 determines a vertical difference between the function $L_{sub}(x)$ between $x_{sub5}$ and $x_{sub6}$ and the straight line $m_1x+c_1$ between $x_{sub5}$ and $x_{sub6}$. In this example, processor 190 also determines a vertical difference between the function $L_{sub}(x)$ between $x_{sub6}$ and $x_{sub7}$ and the straight line $m_2x+c_2$ between $x_{sub6}$ and $x_{sub7}$. An example of a vertical difference between a value of $L_{gas}(x)$ and straight line 936 is a distance 970 shown in FIG. 7. Another example of a vertical difference between a value of $L_{sulphuric}(x)$ and straight line 958 is a distance 972 shown in FIG. 8.

Processor 190 calculates 976 a relative molecular interference function $s_{relative}(x)$ as an antilog, which is an exponent of the difference between the function $L_{sub}(x)$ and the set of straight lines $m_1x+c_1$ and $m_2x+c_2$. The relative molecular interference function $s_{relative}(x)$ is a characteristic function used to identify substance 82 and is a ratio of a molecular interference $s_{sub}(x)$ of substance 82 to a molecular interference function $s_{calib}(x)$ of the calibration substance. The characteristic function is obtained by scanning substance 82 using system 10 (shown in FIG. 1), which is an example of an X-ray system.

Figure 9:
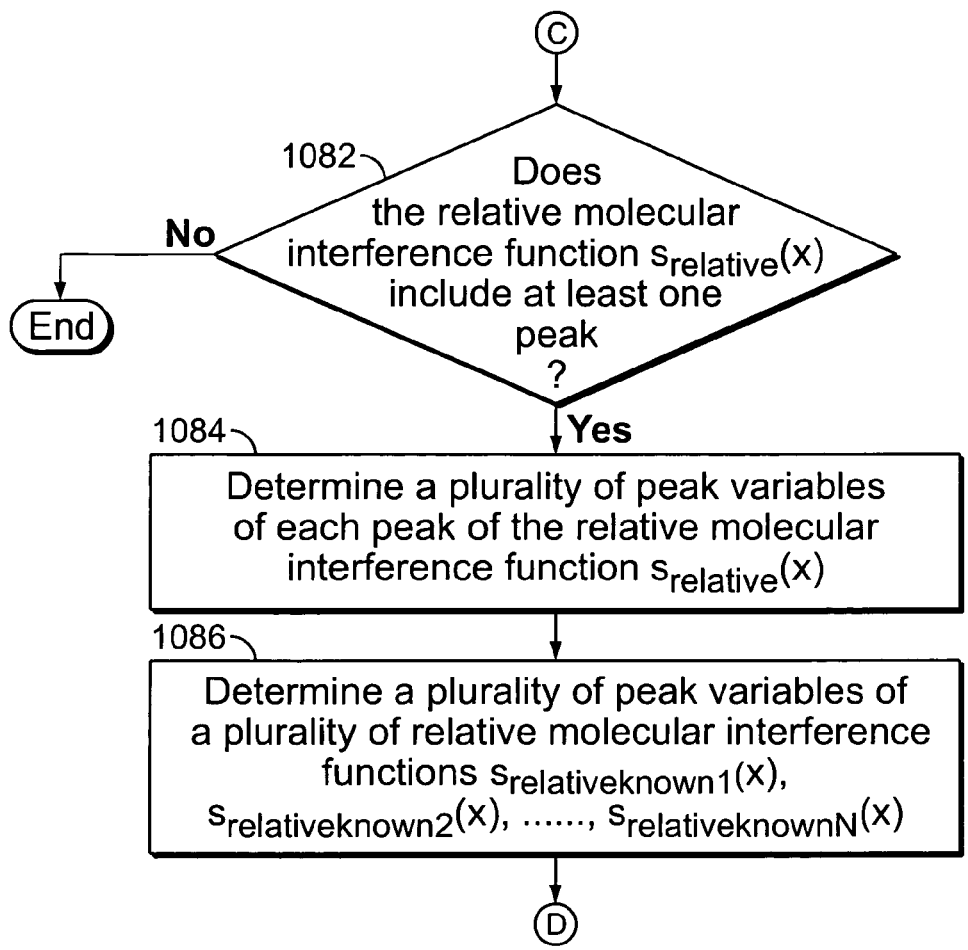
Figure 10:
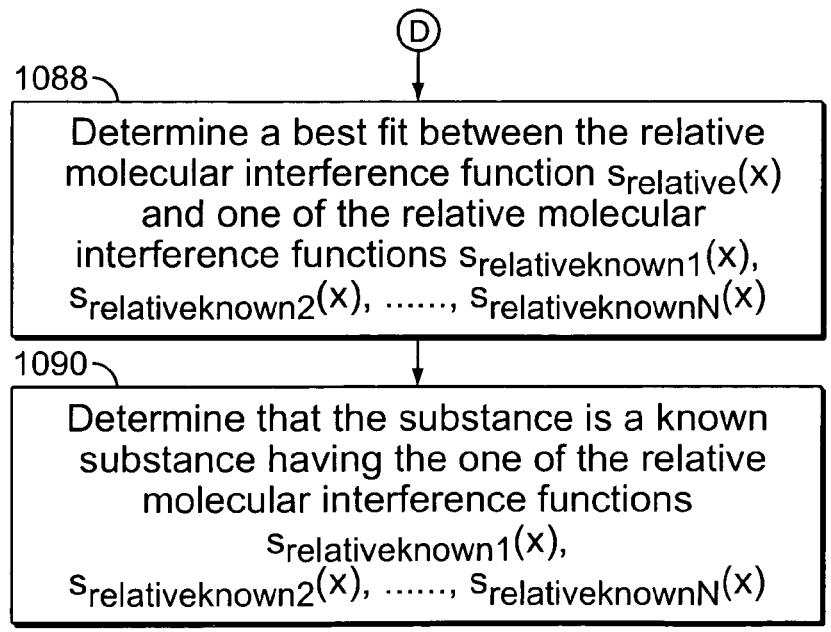
Figure 11:
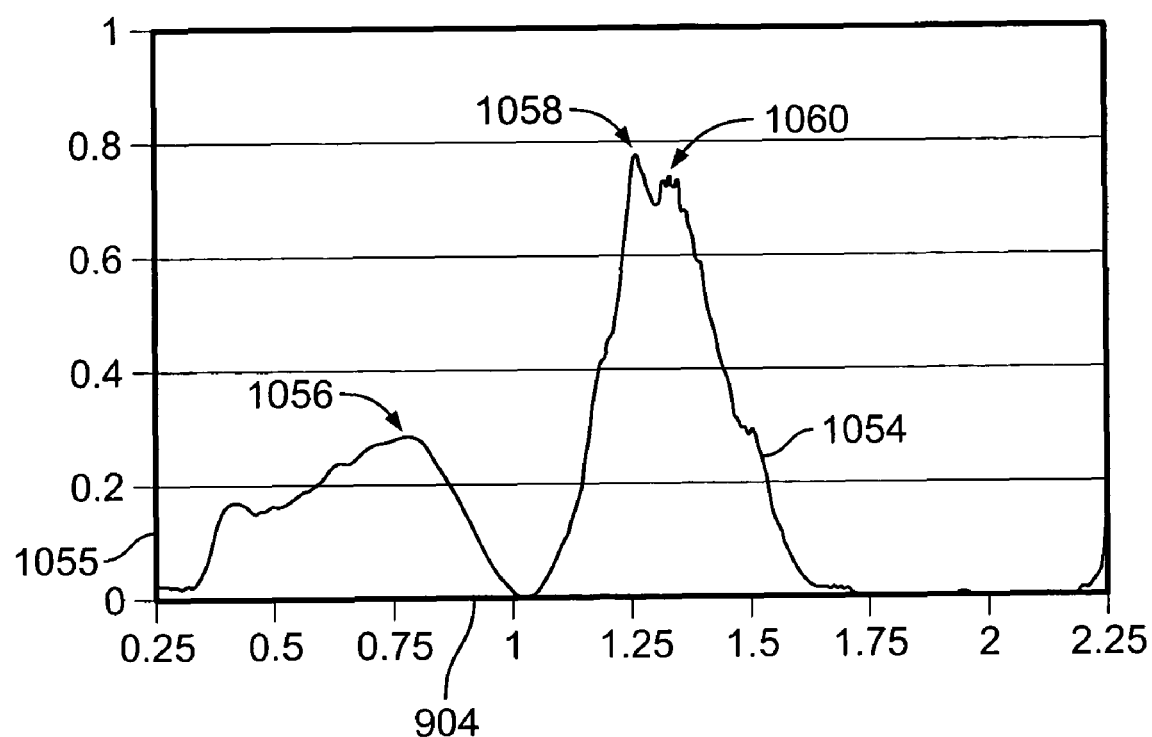

FIGS. 9 and 10 are a flowchart of an embodiment of a method for improving an accuracy of identification of a substance and FIG. 11 is an embodiment of a graph 1054 of a relative molecular interference function. FIG. 9 is also a continuation of the flowchart of FIG. 6. A plurality of relative molecular interference values are plotted on an ordinate 1055. Graph 1054 includes a plurality of peaks 1056, 1058, and 1060. Graph 1054 is an example of the relative molecular interference function $s_{relative}(x)$ plotted as a function of the momentum transfer x on abscissa 904. Referring to FIGS. 1 and 11, graph 1054 is a relative molecular interference function of whisky, which is an example of a substance 82 that may be x-rayed within a container 79.

Referring back to FIG. 9, processor 190 determines 1082 whether the relative molecular interference function $s_{relative}(x)$ of substance 82 includes at least one peak. Upon determining that the relative molecular interference function $s_{relative}(x)$ does not include at least one peak, processor 190 ends the method for improving an accuracy of identification of a substance. On the other hand, upon determining that the relative molecular interference function $s_{relative}(x)$ includes at least one peak, processor 190 determines 1084 a plurality of peak variables of each peak, such as peaks 1056, 1058, and 1060 (shown in FIG. 11), of the relative molecular interference function $s_{relative}(x)$. For example, processor 190 determines at least one of a peak width, a peak amplitude, a peak shape, and a peak position of the at least one peak of the relative molecular interference function $s_{relative}(x)$ upon determining that the relative molecular interference function $s_{relative}(x)$ includes the at least one peak. As another example, if the at least one peak includes a plurality of peaks, processor 190 determines at least one of a set of peak widths, a set of peak amplitudes, a set of peak shapes, and a set of peak positions of the peaks of the relative molecular interference function $s_{relative}(x)$ upon determining that the relative molecular interference function $s_{relative}(x)$ includes the at least one peak. Non-limiting examples of the peak variables include a peak amplitude, a peak width, a peak position, and a peak shape. The relative interference function $s_{relative}(x)$ is represented as a sum of peaks having a plurality of peak amplitudes, peak widths, peak shapes, and peak positions. Processor 190 determines a peak amplitude as a value of the relative molecular interference function $s_{relative}(x)$ at a momentum transfer value at which a second derivative of the molecular interference function $s_{relative}(x)$ is zero. Processor 190 determines a peak width as a full width at half maximum. For example, processor 190 determines a width of peak 1058 (shown in FIG. 11) as a distance between momentum transfer values at which an amplitude is equal to half of an amplitude of the peak. As another example, processor 190 determines a width of peak 1056 (shown in FIG. 11) as a distance between momentum transfer values at which an amplitude is equal to half of an amplitude of the peak. Processor 190 determines a peak position as a momentum transfer value at which the second derivative of the relative molecular interference function $s_{relative}(x)$ is zero.

Processor 190 determines at least one peak shape of the at least one peak of the relative molecular interference function $s_{relative}(x)$ as a function of a Lorentzian function and a Gaussian function. For example, processor 190 determines a peak shape of each peak of the relative molecular interference function $s_{relative}(x)$ as a function of the Lorentzian function and the Gaussian function. As another example, processor 190 determines a plurality of points of each peak of the relative molecular interference function $s_{relative}(x)$ as $$P_s = M\left(\frac{1}{(x-\bar{x}_L)^2 + b_L^2}\right) + N\left(\frac{e^{(-(x-\bar{x}_G)/b_G)^2}}{\sigma\sqrt{2\pi}}\right) \quad \text{Eq. (4)}$$

where M is a Lorentzian amplitude of a Lorentzian component of the peak of the relative molecular interference function $s_{relative}(x)$, N is a Gaussian amplitude of a Gaussian component of the peak of the relative molecular interference function $s_{relative}(x)$, $$\left(\frac{1}{(x-\bar{x}_L)^2 + b_L^2}\right)$$

represents the Lorentzian function, $$M\left(\frac{1}{(x-\bar{x}_L)^2 + b_L^2}\right)$$

represents the Lorentzian component, $$\left(\frac{e^{(-(x-\bar{x}_G)/b_G)^2}}{\sigma\sqrt{2\pi}}\right)$$

represents the Gaussian function, $$N\left(\frac{e^{(-(x-\bar{x}_G)/b_G)^2}}{\sigma\sqrt{2\pi}}\right)$$

represents the Gaussian component, $\bar{x}_L$ is a momentum transfer value of a peak position at which Lorentzian function has a maximum amplitude, $b_L$ is a measure of full width at half maximum of the Lorentzian function, x of the numerator of Equation (4) represents a plurality of momentum transfer values of the Lorentzian function, $\bar{x}_G$ is a momentum transfer value of a peak position at which the Gaussian function has a maximum amplitude, $b_G$ is a measure of full width at half maximum of the Gaussian function, $\sigma$ is a standard deviation of the Gaussian function and is equal to $b_G/\sqrt{2}$, x of the denominator of Equation (4) represents a plurality of momentum transfer values of the Gaussian function. A user provides the Lorentzian and Gaussian functions to processor 190 via input device 192. Processor 190 determines the amplitudes M and N for each peak, such as peaks 1056, 1058, and 1060, of the relative molecular interference function $s_{relative}(x)$ by applying Equation (4) to a plurality of points of the peak, to the Gaussian function, and to the Lorentzian function, and processor 190 further determines a peak shape of the peak as a ratio of the amplitudes M/N. Processor 190 decomposes a peak of the relative molecular interference function $s_{relative}(x)$ into the Lorentzian component and the Gaussian component by representing the peak as a sum of the Gaussian and the Lorentzian components. The sum of the Gaussian and the Lorentzian components is represented by Equation (4).

Processor 190 generates a plurality of diffraction profiles $D_{known2}(x), D_{known3}(x) \ldots D_{knownN}(x)$ of the known substances with effective atomic numbers $Z_{known2}, Z_{known3}, \ldots, Z_{knownN}$ in the same manner as that of determining the diffraction profile $D_{known1}(x)$ of the known substance with the effective atomic number $Z_{known1}$. Processor 190 determines 1086 a plurality of peak variables of a plurality of relative molecular interference functions $s_{relativeknown1}(x)$, $s_{relativeknown2}(x), s_{relativeknown3}(x) \ldots s_{relativeknownN}(x)$ of the known substances with the effective atomic numbers $Z_{known1}$, $Z_{known2}, \ldots, Z_{knownN}$ from the diffraction profiles $D_{known1}(x)$, $D_{known2}(x), D_{known3}(x) \ldots D_{knownN}(x)$ in the same manner as that of determining the relative molecular interference function $s_{relative}(x)$ of substance 82 from the diffraction profiles 900 and 901 (shown in FIG. 4). For example, processor 190 executes 903, 905, 914, 916, 930, 940, 942, 950, 952, 962, 966, and 976 (shown in FIGS. 3, 5, and 6) on a plurality of electrical output signals generated by scanning the known substance with the effective atomic number $Z_{known2}$ to generate the relative molecular interference function $s_{relativeknown2}(x)$. The known substances with the effective atomic numbers $Z_{known1}, Z_{known2} \ldots Z_{knownN}$ are known to a user at a time of scanning the substances using system 10. For example, a user knows that a substance with the effective atomic number $Z_{known1}$ includes a mixture of whisky and water at a time of scanning the mixture using system 10.

Processor 190 determines 1086 a plurality of peak variables, such as peak amplitudes $pa_{11}$, and $pa_{12}$, peak widths $pw_{11}$ and $pw_{12}$, peak positions $pp_{11}$ and $pp_{12}$, and peak shapes $ps_{11}$, and $ps_{12}$, of a plurality of peaks of the relative momentum transfer function $s_{relativeknown1}(x)$ in the same manner as that of determining the peak variables of each of peaks of the relative molecular interference function $s_{relative}(x)$. For example, processor 190 determines the peak amplitude $pa_{11}$ in the same manner as that of determining the peak amplitude of each of peaks 1056, 1058, and 1060. As another example, processor 190 determines the peak width $pw_{12}$ in the same manner as that of determining the peak width of each of peaks 1056, 1058, and 1060 (shown in FIG. 11). As yet another example, processor 190 determines the peak position $pp_{12}$ in the same manner as that of determining the peak position of each of peaks 1056, 1058, and 1060. As still another example, processor 190 determines the peak shape $ps_{11}$ in the same manner as that of determining the peak shape of each of peaks 1056, 1058, and 1060. In the example, processor 190 determines the peak shape as a ratio, such as the ratio M/N, in the same manner as that of determining the ratio M/N. The peak position $pp_{11}$, the peak amplitude $pa_{11}$, the peak width $pw_{11}$, and the peak shape $ps_{11}$ are that of a first peak of the relative molecular interference function $s_{relativeknown1}(x)$, and the peak position $pp_{12}$, the peak amplitude $pa_{12}$, the peak width $pw_{12}$, and the peak shape $ps_{12}$ are that of a second peak of the relative molecular interference function $s_{relativeknown1}(x)$.

Processor 190 also determines 1086 a plurality of peak variables of a plurality of peaks of the relative molecular interference functions $s_{relativeknown2}(x), s_{relativeknown3}(x) \ldots$ $s_{relativeknownN}(x)$. A table listing the peak variables of the peaks of the relative molecular interference functions $s_{relativeknown2}(x), s_{relativeknown3}(x) \ldots s_{relativeknownN}(x)$ is provided below.

TABLE I

| Relative Molecular Interference Function | Peak Amplitudes | Peak Positions | Peak Widths | Peak Shapes |
|---|---|---|---|---|
| $s_{relativeknown2}(x)$ | $pa_{21}, pa_{22}$ | $pp_{21}, pp_{22}$ | $pw_{21}, pw_{22}$ | $ps_{21}, ps_{22}$ |
| $s_{relativeknown3}(x)$ | $pa_{31}, pa_{32}$ | $pp_{31}, pp_{32}$ | $pw_{31}, pw_{32}$ | $ps_{31}, ps_{32}$ |
| ... | ... | ... | ... | ... |
| $s_{relativeknownN}(x)$ | $pa_{N1}, pa_{N2}$ | $pp_{N1}, pp_{N2}$ | $pw_{N1}, pw_{N2}$ | $ps_{N1}, ps_{N2}$ |

The peak amplitude $pa_{N1}$ is an amplitude of a first peak of the relative molecular interference function $s_{relativeknownN}(x)$ and the peak amplitude $pa_{N2}$ is an amplitude of a second peak of the relative molecular interference function $s_{relativeknownN}(x)$. The peak width $pw_{N1}$ is a width of a first peak of the relative molecular interference function $s_{relativeknownN}(x)$ and the peak width $pw_{N2}$ is a width of a second peak of the relative molecular interference function $s_{relativeknownN}(x)$. The peak position $pp_{N1}$ is a position of a first peak of the relative molecular interference function $s_{relativeknownN}(x)$ and the peak position $pp_{N2}$ is a position of a second peak of the relative molecular interference function $s_{relativeknownN}(x)$. The peak shape $ps_{N1}$ is a shape of a first peak of the relative molecular interference function $s_{relativeknownN}(x)$ and the peak shape $ps_{N2}$ is a peak shape of a second peak of the relative molecular interference function $s_{relativeknownN}(x)$.

Processor 190 determines 1088 a best fit between the relative molecular interference function $s_{relative}(x)$ and one of the relative molecular interference functions $s_{relativeknown1}(x)$, $s_{relativeknown2}(x), s_{relativeknown3}(x) \ldots s_{relativeknownN}(x)$. For example, processor 190 determines that peak 1056 fits best with the first peak of the relative molecular interference function $s_{relativeknown1}(x)$ than with the remaining peaks of the remaining relative molecular interference functions $s_{relativeknown1}(x), s_{relativeknown2}(x) \ldots s_{relativeknownN}(x)$. As another example, processor 190 determines that peak 1058 fits best with the second peak of the relative molecular interference function $s_{relativeknown1}(x)$ than with the remaining peaks of the remaining relative molecular interference functions $s_{relativeknown1}(x), s_{relativeknown2}(x) \ldots s_{relativeknownN}(x)$. As yet another example, processor 190 determines that peak 1056 fits best with the first peak of the relative molecular interference function $s_{relativeknown1}(x)$ than with the remaining peaks of the remaining relative molecular interference functions $s_{relativeknown1}(x), s_{relativeknown2}(x) \ldots s_{relativeknownN}(x)$, and determines that peak 1058 fits best with the second peak of the relative molecular interference function $s_{relativeknown1}(x)$ than with the remaining peaks of the remaining relative molecular interference functions $s_{relativeknown1}(x), s_{relativeknown2}(x) \ldots s_{relativeknownN}(x)$. As still another example, processor 190 determines that all peaks, such as, peaks 1056, 1058, and 1060, fit best with all respective peaks, such as, the first peak, the second peak, and a third peak, of the relative molecular interference function $s_{relativeknown1}(x)$ than with the remaining peaks of the remaining relative molecular interference functions $s_{relativeknown2}(x) \ldots s_{relativeknownN}(x)$.

Processor 190 determines that peak 1056 fits best with the first peak of the relative molecular interference function $s_{relativeknown1}(x)$ than with the remaining peaks of the remaining relative molecular interference functions $s_{relativeknown1}(x), s_{relativeknown2}(x) \ldots s_{relativeknownN}(x)$ by determining that the peak variables of peak 1056 are closest to the peak variables of the first peak of the relative molecular interference function $s_{relativeknown1}(x)$ than to the peaks variables of the remaining peaks of the relative molecular interference functions $s_{relativeknown1}(x)$, $s_{relativeknown2}(x)$ ... $s_{relativeknownN}(x)$. For example, processor 190 determines that peak 1056 fits best with the first peak of the relative molecular interference function $s_{relativeknown1}(x)$ than with the remaining peaks of the relative molecular interference functions $s_{relativeknown1}(x)$, $s_{relativeknown2}(x)$ ... $s_{relativeknownN}(x)$ by determining that the peak amplitude of peak 1056 is closest to the peak amplitude of the first peak of the relative molecular interference function $s_{relativeknown1}(x)$ than to the peak amplitudes of the remaining peaks of the relative molecular interference functions $s_{relativeknown1}(x)$, $s_{relativeknown2}(x)$ ... $s_{relativeknownN}(x)$. Moreover, in the example, processor 190 determines that peak 1056 fits best with the first peak of the relative molecular interference function $s_{relativeknown1}(x)$ than with the remaining peaks of the relative molecular interference functions $s_{relativeknown1}(x)$, $s_{relativeknown2}(x)$ ... $s_{relativeknownN}(x)$ by determining that the peak shape, represented by the ratio M/N, of peak 1056 is closest to the peak shape, represented by a ratio, such as, M/N, of the first peak of the relative molecular interference function $s_{relativeknown1}(x)$ than to the peak shapes, represented by a plurality of ratios, such as, M/N, of the remaining peaks of the relative molecular interference functions $s_{relativeknown1}(x)$, $s_{relativeknown2}(x)$ ... $s_{relativeknownN}(x)$.

Furthermore, in the example, processor 190 determines that peak 1056 fits best with the first peak of the relative molecular interference function $s_{relativeknown1}(x)$ than with the remaining peaks of the relative molecular interference functions $s_{relativeknown1}(x)$, $s_{relativeknown2}(x)$ ... $s_{relativeknownN}(x)$ by determining that the peak width of peak 1056 is closest to the peak width of the first peak of the relative molecular interference function $s_{relativeknown1}(x)$ than to the peak widths of the remaining peaks of the relative molecular interference functions $s_{relativeknown1}(x)$, $s_{relativeknown2}(x)$ ... $s_{relativeknownN}(x)$. Moreover, in the example, processor 190 determines that peak 1056 fits best with the first peak of the relative molecular interference function $s_{relativeknown1}(x)$ than with the remaining peaks of the relative molecular interference functions $s_{relativeknown1}(x)$, $s_{relativeknown2}(x)$ ... $s_{relativeknownN}(x)$ by determining that the peak position of peak 1056 is closest to the peak position of the first peak of the relative molecular interference function $s_{relativeknown1}(x)$ than to the peak positions of the remaining peaks of the relative molecular interference functions $s_{relativeknown1}(x)$, $s_{relativeknown2}(x)$ ... $s_{relativeknownN}(x)$. In the example, processor 190 may determine that the peak shape of peak 1056 is closest to the peak shape of the first peak of the relative molecular interference function $s_{relativeknown1}(x)$ than to the peak shapes of the remaining peaks of the relative molecular interference functions $s_{relativeknown1}(x)$, $s_{relativeknown2}(x)$ ... $s_{relativeknownN}(x)$ by determining that the ratio M/N representing a peak shape of peak 1056 is closest to a ratio, such as the ratio M/N, representing the peak shape of the first peak of the relative molecular interference function $s_{relativeknown1}(x)$ than to the remaining ratios, such as the ratio M/N, representing the peak shapes of the remaining peaks of the remaining relative molecular interference functions $s_{relativeknown2}(x)$ ... $s_{relativeknownN}(x)$.

Upon determining the best fit between the relative molecular interference function $s_{relative}(x)$ and one of the relative molecular interference functions $s_{relativeknown1}(x)$, $s_{relativeknown2}(x)$, $s_{relativeknown3}(x)$ ... $s_{relativeknownN}(x)$, processor 190 determines 1090 that substance 82 is the known substance having the one of the relative molecular interference functions $s_{relativeknown1}(x)$, $s_{relativeknown2}(x)$, $s_{relativeknown3}(x)$ ... $s_{relativeknownN}(x)$. Accordingly, processor 190 identifies substance 82 as one of the known substances with one of the corresponding effective atomic numbers $Z_{known1}$, $Z_{known2}$, ..., $Z_{knownN}$ and the one of the known substances has one of the relative molecular interference functions $s_{relativeknown1}(x)$, $s_{relativeknown2}(x)$, $s_{relativeknown3}(x)$ ... $s_{relativeknownN}(x)$ that is best fitted with the relative molecular interference function $s_{relative}(x)$. Hence, processor 190 identifies substance 82 upon determining at least one of a peak width, a peak amplitude, a peak shape, and a peak position of the at least one peak of the characteristic function.

In an alternative embodiment, at least one of the relative molecular interference functions $s_{relativeknown1}(x)$, $s_{relativeknown2}(x)$, $s_{relativeknown3}(x)$ ... $s_{relativeknownN}(x)$ has at least one peak. For example, one of the relative molecular interference functions $s_{relativeknown1}(x)$, $s_{relativeknown2}(x)$, $s_{relativeknown3}(x)$ ... $s_{relativeknownN}(x)$ has more than two peaks. In another alternative embodiment, any of the relative molecular interference functions $s_{relativeknown1}(x)$, $s_{relativeknown2}(x)$, $s_{relativeknown3}(x)$ ... $s_{relativeknownN}(x)$ may not include a peak.

In yet another alternative embodiment, processor 190 determines that peak 1056 fits best with the first peak of the relative molecular interference function $s_{relativeknown1}(x)$ than with the remaining peaks of the remaining relative molecular interference functions $s_{relativeknown1}(x)$, $s_{relativeknown2}(x)$ ... $s_{relativeknownN}(x)$ by determining that at least one of the peak variables of peak 1056 are closest to at least one of the corresponding peak variables of the relative molecular interference function $s_{relativeknown1}(x)$ than to at least one of the corresponding peak variables of the remaining peaks of the relative molecular interference functions $s_{relativeknown1}(x)$, $s_{relativeknown2}(x)$ ... $s_{relativeknownN}(x)$. For example, processor 190 determines that peak 1056 fits best with the first peak of the relative molecular interference function $s_{relativeknown1}(x)$ than with the remaining peaks of the relative molecular interference functions $s_{relativeknown1}(x)$, $s_{relativeknown2}(x)$ ... $s_{relativeknownN}(x)$ by determining that the peak amplitude of peak 1056 is closest to the peak amplitude of the first peak of the relative molecular interference function $s_{relativeknown1}(x)$ than to the peak amplitudes of the remaining peaks of the relative molecular interference functions $s_{relativeknown1}(x)$, $s_{relativeknown2}(x)$ ... $s_{relativeknownN}(x)$.

As another example, processor 190 determines that peak 1056 fits best with the first peak of the relative molecular interference function $s_{relativeknown1}(x)$ than with the remaining peaks of the relative molecular interference functions $s_{relativeknown1}(x)$, $s_{relativeknown2}(x)$ ... $s_{relativeknownN}(x)$ by determining that the peak shape of peak 1056 is closest to the peak shape of the first peak of the relative molecular interference function $s_{relativeknown1}(x)$ than to the peak shapes of the remaining peaks of the relative molecular interference functions $s_{relativeknown1}(x)$, $s_{relativeknown2}(x)$ ... $s_{relativeknownN}(x)$. Moreover, in the example, processor 190 determines that peak 1056 fits best with the first peak of the relative molecular interference function $s_{relativeknown1}(x)$ than with the remaining peaks of the relative molecular interference functions $s_{relativeknown1}(x)$, $s_{relativeknown2}(x)$ ... $s_{relativeknownN}(x)$ by determining that the peak position of peak 1056 is closest to the peak position of the first peak of the relative molecular interference function $s_{relativeknown1}(x)$ than to the peak positions of the remaining peaks of the relative molecular interference functions $s_{relativeknown1}(x)$, $s_{relativeknown2}(x)$ ... $s_{relativeknownN}(x)$.

In another alternative embodiment, a user provides a plurality of data points representing the Gaussian and the Lorentzian functions, and processor 190 determines, from the data points, the maximum amplitude of the Lorentzian function in the same manner as that of determining a peak amplitude of any of peaks of the relative molecular interference function $s_{relative}(x)$. In this embodiment, processor 190 determines the momentum transfer value $\bar{x}_L$ as a momentum transfer value corresponding to the maximum amplitude of the Lorentzian function. In this embodiment, processor 190 determines in the same manner as that of determining a full width at half maximum of any of peaks of the relative molecular interference function $s_{relative}(x)$. In this embodiment, processor 190 determines, from the data points, the maximum amplitude of the Gaussian function. In this embodiment, processor 190 determines the momentum transfer value $\bar{x}_G$ at the maximum amplitude of the Gaussian function. In this embodiment, processor 190 determines the full width at half maximum $b_G$ in the same manner as that of determining a peak width of any peak of the relative molecular interference function $s_{relative}(x)$. In this embodiment, processor 190 determines the standard deviation $\sigma$ of the Gaussian function.

Techniques illustrated in FIGS. 3, 5, 6, 9, and 10, in some instances, may be performed sequentially, in parallel, or in an order other than that which is described. For example, the technique of 905 (shown in FIG. 3) may be performed before performing the technique of 903. It should be appreciated that not all of the techniques described are required to be performed, that additional techniques may be added, and that some of the illustrated techniques may be substituted with other techniques.

A technical effect of the herein described methods, a processor, and a system for improving an accuracy of identification of a substance includes using at least a plurality of values of the function $L_{sub}(x)$ in a range from and including the momentum transfer value $x_{sub5}$ to the momentum transfer value $x_{sub6}$ to determine the effective atomic number $Z_{effsub}$ of substance 82 (shown in FIG. 1). The plurality of values of the function $L_{sub}(x)$ helps average a plurality of oscillations in a molecular interference function determined by other techniques. The plurality of values of the function $L_{sub}(x)$ represents a greater number of photons than a number of photons represented by a plurality of values of the diffraction profile $D_{sub}(x)$ within the range from and including $x_{sub1}$ to $x_{sub3}$. The greater number of photons provides a better estimate of the effective atomic number $Z_{effsub}$ than that provided by using the value of the diffraction profile $D_{sub}(x)$ within the range from and including $x_{sub1}$ to $x_{sub3}$.

The greater number of photons reduces an amount of noise that adversely affects a calculation of an effective atomic number of substance 82 (shown in FIG. 1). The greater number of photons facilitates reducing any increase in the noise due to variations in a spectrum of intensities of X-rays output by X-ray source 12, any non-uniformity in efficiency of detection of primary beams 83 and 84 and scattered rays 88, 89, 90, 91 by scatter detectors 16 and 18, and/or any variation in incident angles 96, 97, 98, and 105 (shown in FIG. 1). Moreover, the greater number of photons facilitates reducing false alarms in characterizing substance 82 and enhances a detection rate of characterizing substance 82.

Another technical effect includes using a plurality of values of the function $L_{sub}(x)$ between the momentum transfer values $x_{sub5}$ and $x_{sub7}$ to determine the relative molecular interference function $s_{relative}(x)$. The plurality of values of the function $L_{sub}(x)$ represents a number of photons greater than a number of photons represented by values of the diffraction profile $D_{sub}(x)$ between the ranges from and including $x_{sub1}$ to $x_{sub3}$ and facilitates generation of a better approximation of the molecular interference function $s_{sub}(x)$ and than that generated by using the values of the diffraction profile $D_{sub}(x)$. Substance 82 can be characterized more accurately based on the more accurate values of $Z_{effsub}$ and $s_{relative}(x)$.

Another technical effect includes improving an accuracy of identification of substance 82 based on a best fit between the relative molecular interference function $s_{relative}(x)$ and one of the relative molecular interference functions $s_{relativeknown1}(x)$, $s_{relativeknown2}(x)$ ... and $s_{relativeknownN}(x)$. Yet another technical effect includes using a peak shape of a peak of the relative molecular interference function $s_{relative}(x)$ to identify substance 82, and decomposing the peak into the Lorentzian and Gaussian components. The decomposition helps identify substance 82 based on a peak variable of a peak of the characteristic function of substance 82. For example, the decomposition helps identify substance 82 based on a peak shape of a peak of the relative molecular interference function $s_{relative}(x)$. The use of a peak shape of a peak of the relative molecular interference function $s_{relative}(x)$ to identify substance 82 provides a more accurate identification of substance 82 compared to an identification without using the peak shape.

Exemplary embodiments of methods, a processor, and a system for improving an accuracy of identification of a substance are described above in detail. The methods, a processor, and a system are not limited to the specific embodiments described herein. For example, the methods and the processor may be used in combination with other inspection/detection systems. Additionally, unless otherwise indicated, one or more elements of one Figure may be referenced in combination with one or more elements of any of the other Figures.

While various embodiments of the invention have been described, those skilled in the art will recognize that modifications of these various embodiments of the invention can be practiced within the spirit and scope of the claims.

What is claimed is:

1. A method for improving an accuracy of identification of a substance, said method comprising determining, using a processor, whether a relative molecular interference function of the substance includes at least one peak, the relative molecular interference function representing a ratio of a molecular interference function of the substance to a molecular interference function of a calibration substance.

2. A method in accordance with claim 1, further comprising determining at least one of a peak width, a peak amplitude, a peak shape, and a peak position of the at least one peak of the relative molecular interference function upon determining that the relative molecular interference function includes the at least one peak.

3. A method in accordance with claim 2, further comprising determining the peak shape as a function of a Lorentzian function and a Gaussian function.

4. A method in accordance with claim 1, wherein the at least one peak includes a peak, said method further comprising decomposing the peak into a Lorentzian component and a Gaussian component.

5. A method in accordance with claim 1, wherein the at least one peak includes a plurality of peaks, said method further comprising determining at least one of a set of peak widths, a set of peak amplitudes, a set of peak shapes, and a set of peak positions of the peaks of the relative molecular interference function upon determining that the relative molecular interference function includes the at least one peak.

6. A processor configured to determine whether a relative molecular interference function of a substance includes at least one peak, the relative molecular interference function representing a ratio of a molecular interference function of the substance to a molecular interference function of a calibration substance.

7. A processor in accordance with claim 6, wherein said processor is further configured to determine at least one of a peak width, a peak amplitude, a peak shape, and a peak position of the at least one peak of the relative molecular interference function upon determining that the relative molecular interference function includes the at least one peak.

8. A processor in accordance with claim 7, wherein said processor is further configured to determine the peak shape as a function of a Lorentzian function and a Gaussian function.

9. A processor in accordance with claim 6, wherein the at least one peak includes a peak, and said processor is further configured to decompose the peak into a Lorentzian component and a Gaussian component.

10. A processor in accordance with claim 6, wherein the at least one peak includes a plurality of peaks, said processor is further configured to determine at least one of a set of peak widths, a set of peak amplitudes, a set of peak shapes, and a set of peak positions of the peaks of the relative molecular interference function upon determining that the relative molecular interference function includes the at least one peak.

11. A system for improving an accuracy of identification of a substance, said system comprising:
an X-ray source configured to generate X-rays;
a detector operatively coupled to said X-ray source, and configured to detect the X-rays and output an electrical signal representative of the detected X-rays; and
a processor coupled to said detector and configured to determine whether a relative molecular interference function of the substance includes at least one peak, the relative molecular interference function representing a ratio of a molecular interference function of the substance to a molecular interference function of a calibration substance.

12. A system in accordance with claim 11, wherein said processor is further configured to determine at least one of a peak width, a peak amplitude, a peak shape, and a peak position of the at least one peak of the relative molecular interference function upon determining that the relative molecular interference function includes the at least one peak.

13. A system in accordance with claim 12, wherein said processor is further configured to determine the peak shape as a function of a Lorentzian function and a Gaussian function.

14. A system in accordance with claim 11, wherein the at least one peak includes a peak, and wherein said processor is further configured to decompose the peak into a Lorentzian component and a Gaussian component.

15. A system in accordance with claim 11, wherein the at least one peak includes a plurality of peaks, said processor is further configured to determine at least one of a set of peak widths, a set of peak amplitudes, a set of peak shapes, and a set of peak positions of the peaks of the relative molecular interference function upon determining that the relative molecular interference function includes the at least one peak.

16. A method for improving an accuracy of identification of a substance, said method comprising identifying the substance, using a processor, based on a peak variable of a peak of a relative molecular interference function of the substance, the relative molecular interference function representing a ratio of a molecular interference function of the substance to a molecular interference function of a calibration substance.

17. A method in accordance with claim 16, further comprising identifying the substance upon determining at least one of a peak width, a peak amplitude, a peak shape, and a peak position of the peak of the relative molecular interference function.

18. A method in accordance with claim 17, further comprising determining the peak shape as a function of a Lorentzian function and a Gaussian function.

19. A method in accordance with claim 16, further comprising decomposing the peak into a Lorentzian component and a Gaussian component.

20. A method in accordance with claim 16, further comprising obtaining the relative molecular interference function by scanning the substance using an X-ray system.

* * * * *